United States Patent [19]
Paulus et al.

[11] Patent Number: 6,011,176
[45] Date of Patent: Jan. 4, 2000

[54] USING ANIONIC FLOCCULANTS FOR ORGANIC-AQUEOUS PHASE SEPARATION

[75] Inventors: Wolfgang Paulus, Mainz; Matthias Geisendörfer, Neustadt, both of Germany

[73] Assignee: BASF Aktiengesellschaft, Ludwigshafen, Germany

[21] Appl. No.: 09/239,971

[22] Filed: Jan. 29, 1999

[30] Foreign Application Priority Data

Jan. 30, 1998 [DE] Germany .............. 198 03 658

[51] Int. Cl.$^7$ .................................................. C07C 51/42
[52] U.S. Cl. ...................... 562/600; 562/598; 562/599; 560/217; 560/218; 252/358; 252/364
[58] Field of Search ................... 562/598, 599, 562/600; 560/217, 218; 252/358, 364

[56] References Cited

U.S. PATENT DOCUMENTS

| | | | |
|---|---|---|---|
| 3,442,935 | 5/1969 | Pine et al. | 560/205 |
| 4,074,062 | 2/1978 | Murakami et al. | 560/217 |
| 4,715,962 | 12/1987 | Bhattacharyya et al. | 210/708 |
| 5,358,988 | 10/1994 | Schieferstein et al. | 524/280 |
| 5,433,863 | 7/1995 | Braden et al. | 210/708 |
| 5,478,477 | 12/1995 | Ramesh et al. | 210/728 |
| 5,663,263 | 9/1997 | Fischer et al. | 526/318.41 |

FOREIGN PATENT DOCUMENTS

| | | |
|---|---|---|
| 2074501 | 1/1994 | Canada . |
| 0 561 264 | 9/1993 | European Pat. Off. . |
| 1954548 | 5/1971 | Germany . |

OTHER PUBLICATIONS

N.S. Allen, M.a. Johnson, P. Oldrig (ed.) And M.S. Salim, Chemistry & Technology of UV & EB–Curing Formulations for coatings, Inks & Paints, vol. 2, SITA Technology, London 1991 (Table of contents).
JP–09–316,033 (Patent Abstract, Japan vol. 098, No. 004, Mar. 31, 1999).
JP–62–042,948 (Patent Abstract, Japan vol. 011, No. 229, Jul. 25, 1999).

*Primary Examiner*—Paul J. Killos
*Assistant Examiner*—Taylor V. Oh
*Attorney, Agent, or Firm*—Oblon, Spivak, McClelland, Maier & Neustadt, P.C.

[57] ABSTRACT

The use of organic, polymeric, anionic water-soluble flocculants for the phase separation of an organic-aqueous system which essentially comprises monomeric acrylates, diacrylates, (poly)ester acrylates or (poly)ether acrylates and unreacted residues of the carboxylic anhydrides, carboxylic acids or alcohols used for preparing the acrylates.

10 Claims, No Drawings

USING ANIONIC FLOCCULANTS FOR ORGANIC-AQUEOUS PHASE SEPARATION (Poly)ester acrylates, (poly)ether acrylates or monomeric acrylates are normally prepared by esterifying (poly) esterpolyols, (poly)etherpolyols or alkanols with $\alpha,\beta$-ethylenically unsaturated carboxylic acids or their anhydrides. Appropriate preparation techniques are described, for example, in N.S. Allen, M. A. Johnson, P. Oldring (ed.) and M. S. Salim, Chemistry & Technology of UV & EB-Curing Formulations for Coatings, Inks & Paints, Vol. 2, SITA Technology, London 1991.

Esterification is an equilibrium reaction in which the equilibrium is normally shifted in the direction of ester formation by, inter alia, adding the carboxylic acid in excess. Following the esterification, it is usual to remove excess $\alpha,\beta$-ethylenically unsaturated carboxylic acid, whose odor or irritant effect, for example, might impact adversely on the usefulness of the esterification product; the excess acid is removed by distillation or the reaction mixture is washed one or more times with aqueous media.

A serious disadvantage of the washing process, however, is that the organic phase comprising the esterification product is slow to separate from the aqueous phase comprising the excess carboxylic acid. Complete phase separation requires long standing times which may amount to several hours when preparing monomeric acrylates, (poly)ester acrylates or (poly)ether acrylates on the industrial scale. This makes the preparation of these acrylates much more expensive.

In order to accelerate separation of the organic from the aqueous phase, it is common to add what are known as emulsion breakers or demulsifiers. Examples of such emulsion breakers are compounds of low molecular mass, such as salts of fatty acids or sulfonic acids, and the acids themselves, and surface-active products of higher molecular mass, based on adducts of ethylene oxide or propylene oxide. The latter are nonionic compounds, such as the substances marketed under the tradename Separol® by BASF AG, Ludwigshafen, Germany. Experiments carried out by the applicant with such emulsion breakers, however, showed that they do not bring about any acceleration in separation between organic phases which comprise the abovementioned acrylates and aqueous phases which comprise the anhydrides, carboxylic acids or alcohols employed in preparing the acrylate.

The possibility of using flocculants to influence phase separation has not been discussed to date in the prior art. Flocculants are normally employed for entirely different purposes, namely in order to influence a zeta potential of colloidally dissolved particles in such a way that the solid particles flocculate out of the colloidal liquid.

It is an object of the present invention to shorten the phase separation times of organic-aqueous solution systems relative to the prior art in connection with the preparation of monomeric acrylates, (poly)ester acrylates or (poly)ether acrylates.

We have found that this object is achieved by adding an organic, polymeric, anionic water-soluble flocculant, which shortens the separation times between organic phases comprising monomeric acrylates, (poly)ester acrylates or (poly) ether acrylates and aqueous phases, especially the aqueous washing medium used to remove excess reactants in acrylate preparation.

The present invention therefore provides for the use of organic, polymeric, anionic water-soluble flocculants for the phase separation of an organic-aqueous system which essentially comprises monomeric acrylates, diacrylates, organic (poly)ester acrylates or (poly)ether acrylates and unreacted residues of the reactants used for their preparation, especially alcohols and carboxylic acids or carboxylic anhydrides.

The abovementioned organic acrylate components and unreacted fractions of alcohols and carboxylic acids or anhydrides are usually present in dissolved form in the organic-aqueous system. In contrast to the acrylate component, the alcohols or carboxylic acids and anhydrides which are likewise present, however, possess a much higher solubility in aqueous media.

A skilled worker will normally use the terms ester acrylates, ether acrylates or monomeric acrylates even if the starting compounds were esterified not with acrylic acid but with another $\alpha,\beta$-ethylenically unsaturated carboxylic acid. Such terminology is retained in the present invention.

In relation to the prior art, the use provided for by the invention features a number of surprising advantages:

I. The removal of excess $\alpha,\beta$-ethylenically unsaturated carboxylic acid can be accelerated considerably through the shortening in the phase separation times.

II. The use of anionic flocculants increases the achievable yield, since the flocculants cause the formation of a clear phase boundary.

III. The performance properties of the oligo/polyester acrylates or oligo/polyether acrylates, such as formulatability and mechanical properties of the UV-cured films, are not impaired by the addition of anionic flocculants.

Anionic polymers which can be used:

In accordance with the invention it is preferred to use water-soluble anionic flocculants selected from functional, high molecular mass polymers which comprise anionic carboxylic acid, sulfonic acid, phosphoric acid and/or phosphonic acid functions, especially carboxylic acid radicals, in neutralized form or in salt form, alone or together with further polar radicals, such as carboxamide radicals. Anionically modified flocculants which are suitable in accordance with the invention are obtainable with the aid of conventional polymerization processes by copolymerizing at least one ethylenically unsaturated monomer which carries an anionic or anionizable side group and is selected, for example, from acrylic, methacrylic, vinylsulfonic, vinylphosphonic, itaconic and 2-acrylamidomethylpropanesulfonic acid, sulfopropyl acrylate and sulfopropyl methacrylate, with at least one further, nonionic comonomer, which is selected, for example, from acrylamide, methacrylamide, N-vinylformamide, N-vinylacetamide, N-vinylmethylacetamide, N-vinylmethylformamide, vinyl acetate and vinylpyrrolidone. It would also be possible to consider introducing anionic functional groups into the high molecular mass polymer by esterifying carboxyl groups with a polyol, such as ethanediol, and subjecting the remaining free hydroxyl groups to further reaction with, for example, sulfuric or phosphoric acid. Use is made in particular in accordance with the invention of anionically modified, high molecular mass polyacrylamide, which is obtainable, for example, by copolymerizing (meth)acrylamide and (meth)acrylic acid.

Anionic flocculants which can be used with preference in the context of the present invention have a viscosity in the range from 11 to 13, in particular from 12 to 12.5 mPa.s at a concentration of 0.01% of polymer in fully deionized water, measured with a Contraves Rheomat 30. It is preferred to use anionic flocculants which have a charge density in the range from 1 to 10, in particular from 4 to 9 (milliequivalents of Na acrylate per gram of substance). The molecular weight of the anionic flocculants which can be used with preference is within the range from 4 to 22, in particular from 10 to 20 megadaltons. Particularly suitable flocculants are the anionic products marketed under the tradename Sedipur® by BASF AG, Ludwigshafen, Germany.

The anionic flocculants are preferably used in a concentration of from about 10 to 1000 ppm, with particular preference from about 50 to 200 ppm, based on the aqueous washing medium.

The aqueous component (phase) of the organic-aqueous system preferably comprises ionic compounds, such as alkali metal or alkaline earth metal halides, especially NaCl, $CaCl_2$, $MgSO_4$ or KCl in amounts of from 0.1 to 30, in particular from about 1 to 25% by weight, based on the overall weight of the aqueous component, in order to accelerate phase separation. Preference is also given to adding basic compounds, such as NaOR, $Ca(OH)_2$ or KOH, for example, to the aqueous component in order to neutralize the excess $\alpha,\beta$-ethylenically unsaturated carboxylic acid. The aqueous component represents a washing phase for the organic, acrylate-containing phase. The washing phase can be added to the organic phase one or more times with identical or different composition.

The use of the anionic polymers in accordance with the invention is particularly appropriate where highly soluble acrylates are obtained in the organic phase in a mixture with compounds of better solubility in water, such as carboxylic acid. Examples of this which can be mentioned are:

a) the preparation of polyester and polyether acrylates by condensing $\alpha,\beta$-ethylenically unsaturated carboxylic acids with alkanols, such as polyesterols or polyetherols; such as e.g. of polymers which are marketed under the trade name Laromer® by BASF AG, Ludwigshafen, Germany.

b) the preparation of low molecular mass acrylate compounds in a washing procedure.

Accordingly, different mixtures of substances have to be separated depending on the field of application.

In accordance with a first area of application of the invention, the organic component (phase) of the organic-aqueous system preferably comprises polyester acrylates or polyether acrylates which are obtainable by condensing alkanols, especially polyesterols or polyetherols, with $\alpha,\beta$-ethylenically unsaturated carboxylic acids or their anhydrides, or condensing polyesters which carry terminal carboxyl groups with carboxylic esters which carry hydroxyl groups, in the organic phase. Reactants which can be used to prepare the polyester or polyether acrylates, respectively, are elucidated further in the following sections.

$\alpha,\beta$-ethylenically unsaturated carboxylic acids:

As $\alpha,\beta$-ethylenically unsaturated carboxylic acids and their anhydrides it is possible to employ mono- and/or dicarboxylic acids, eg. acrylic acid, methacrylic acid, fumaric acid, maleic acid, maleic anhydride, crotonic acid, itaconic acid, etc., or mixtures thereof. It is preferred to employ acrylic acid and methacrylic acid.

Polyesterols:

Suitable polyesterols which can be employed are linear or branched polymers having terminal OH groups; for example, those having two OH end groups.

The polyesterols can be simply prepared by esterifying aliphatic, cycloaliphatic and aromatic di-, tri and/or polycarboxylic acids with di-, tri- and/or polyols.

Examples of carboxylic acids suitable for preparing the polyesterols are dicarboxylic acids having 2 to 20 carbon atoms, preferably 4 to 15 carbon atoms, examples of which are malonic acid, succinic acid, adipic acid, glutaric acid, pimelic acid, suberic acid, sebacic acid, dodecanedioic acid, phthalic acid, terephthalic acid, isophthalic acid, cyclohexanedicarboxylic acid, etc. The dicarboxylic acids can be employed individually or as mixtures.

Examples of diols suitable for preparing the polyesterols are glycols, preferably having 2 to 25 carbon atoms. Examples of suitable glycols are 1,2-ethanediol, 1,3-propanediol, 1,4-butanediol, 1,5-pentanediol, 1,6-hexanediol, 1,10-decanediol, diethylene glycol, dipropylene glycol, tripropylene glycol, 2,2,4-trimethyl-1,5-pentanediol, 2,2-dimethyl-1,3-propanediol, 1,4-dimethylolcyclohexane, 1,6-dimethylolcyclohexane and ethoxylated/propoxylated ethers and ethoxylated/propoxylated products of 2,2-bis(4-hydroxyphenyl)propane (bisphenol A), etc. Suitable triols and polyols have, for example, from 3 to 25, preferably 3 to 18 carbon atoms. Examples include glycerol, trimethylolpropane, erythritol, pentaerythritol, sorbitol, etc., and the ethoxylated/propoxylated products thereof. Suitable polyesterols can likewise be prepared by polymerizing lactones—for example, lactones having 3 to 20 carbon atoms. Examples of suitable lactones for preparing the polyesterols are $\alpha,\alpha$-dimethyl-$\beta$-propiolactone, $\gamma$-butyrolactone, $\epsilon$-caprolactone, etc.

In preparing the polyester acrylates it is also possible to employ condensation products based on hydroxyl-containing esters of $\alpha,\beta$-ethylenically unsaturated mono- and/or dicarboxylic acids, especially of acrylic and/or methacrylic acid, with at least divalent alcohols. Examples of these include 2-hydroxyethyl acrylate, 2-hydroxyethyl methacrylate, 2-hydroxypropyl acrylate, 2-hydroxypropyl methacrylate, 3-hydroxybutyl acrylate, 3-hydroxybutyl methacrylate, 4-hydroxybutyl acrylate 4-hydroxybutyl methacrylate, 6-hydroxyhexyl acrylate, 6-hydroxyhexyl methacrylate, 3-hydroxy-2-ethylhexyl acrylate, 3-hydroxy-2-ethylhexyl methacrylate, di(meth)acrylic esters of 1,1,1-trimethylolpropane or of glycerol. These hydroxyl-containing esters can be condensed with polyesters that carry terminal carboxyl groups. Such polyesters are obtainable in a conventional manner by, for example, esterifying the above-mentioned di-, tri- and/or polyols with di-, tri- and/or polycarboxylic acids in excess.

Polyetherols:

As polyetherols it is possible to employ linear or branched substances which have terminal hydroxyl groups, comprise ether bonds and possess a molecular weight in the range from about 250 to 10,000, for example, preferably from 250 to 5000 daltons.

Suitable polyetherols can readily be prepared by polymerizing cyclic ethers, such as tetrahydrofuran, or by reacting one or more alkylene oxides having 2 to 4 carbon atoms in the alkyl radical with a starter molecule which comprises two active hydrogen atoms. Examples that may be mentioned of alkylene oxides are ethylene oxide, 1,2-propylene oxide, epichlorohydrin, 1,2-and 2,3-butylene oxide. The alkylene oxides can be employed individually, successively in alternation or as a mixture. The starter molecule may, for example, comprise water, the above-mentioned glycols or triols, amines, such as ethylenediamine, hexamethylenediamine and 4,4'-diaminodiphenyl-methane, and amino alcohols, such as ethanolamine.

Like the polyesterols, the polyetherols can also be used alone or in mixtures.

The invention is particularly suitable for working up a reaction mixture comprising alkoxylated, especially ethoxylated and/or propoxylated, trimethylolpropane triacrylate having a degree of alkoxylation in the range from 3 to 30.

In a second area of application of the invention the organic component (phase) comprises low molecular mass acrylate esters which can be prepared in a washing procedure from (meth)acrylic acid and (poly)alcohols. Examples are monomeric acrylates, such as tert-butyl cyclohexyl acrylate, lauryl acrylate, 2-ethylhexyl acrylate, decanediol diacrylate, hexanediol diacrylate, butanediol diacrylate, tripropylene glycol diacrylate, dipropylene glycol diacrylate, ethyldiglycol acrylate, neopentyl glycol diacrylate, trimethylolpropane triacrylate, pentaerythritol triacrylate and pentaerythritol tetraacrylate.

Solvents which can be employed in the above-described esterification reactions for preparing the acrylates present in the organic component in the organic-aqueous system are in particular those which are organic, have a boiling point of below 110° C. and form azeotropic mixtures with water. Particularly suitable organic solvents are pentane, hexane, heptane, cyclohexane, methylcyclohexane, cyclopentane, dichloroethane, toluene, xylene, and also ligroin and petroleum ether.

The esterification reaction is preferably conducted in the presence of strong acids as esterification catalysts. Examples of suitable esterification catalysts are sulfuric acid, phosphoric acid, alkylsulfonic acids, arylsulfonic acids or cation exchangers comprising sulfonic acid groups, but especially sulfuric acid and, with particular preference, toluenesulfonic acids.

The concentration of catalyst in the reaction mixture is generally from 0.1 to 10% by weight, preferably from 0.5 to 5% by weight.

The esterification is preferably conducted in the presence of customary polymerization inhibitors or metal salts in an amount of in each case from about 100 to 5000 ppm, based on the reaction mixture, or, if desired, lean air with an $O_2$ content $\leq 6\%$ (from 0.1 to 1000 l per hour.l). The reaction temperature for the esterification is generally from about 70 to 160° C., preferably from 90 to 130° C.

The reaction time for the esterification reaction is generally from 1 to 24, preferably from 1 to 16 and, in particular, from 2 to 12 hours.

The reaction can be conducted under atmospheric, subatmospheric or superatmospheric pressure. The pressure is preferably established such that the water formed during the esterification is removed by distillation in the form, for example, of an azeotropic mixture of water and organic solvent, with the organic component preferably being recycled to the esterification. The esterification can be conducted continuously or discontinuously, the latter regime being preferred.

Esterification is conducted in customary apparatus; for example, in an esterification unit comprising one or more heatable stirred reactors (cascade) which may or may not be fitted with columns, condensers and phase separation vessels. The reactor contents are mixed by stirring, forced circulation or other customary and suitable means.

The reaction mixture obtained following esterification is freed from excess α,β-ethylenically unsaturated carboxylic acid by one or more washing steps in the presence of an anionic flocculent as described above. For instance, a three-stage washing step can be performed by washing the reaction mixture from the esterification first of all with an aqueous phase comprising NaCl, then neutralizing it with an aqueous phase comprising NaOH and finally, washing it again with an aqueous medium comprising NaCl.

Before each washing step it is preferable to add the particular amount of organic flocculant to the aqueous washing medium and only then to add the washing medium, containing the flocculant, to the reaction mixture obtained following the esterification. Alternatively, the flocculant can be added directly to the aqueous-organic system. The organic flocculant to be employed can be added all at once in a single portion or else metered in slowly. The aqueous-organic system obtained after each washing step is left to rest each time until phase separation has taken place. This phase separation is accelerated considerably by the novel use of the anionic flocculant.

The washing operation is conducted in general in a customary extraction apparatus; for example in a stirred vessel or washing vessel, a column without energy input, a pulsed column, a column with a rotating insert, a mixer/settler apparatus or a centrifugal extractor, preferably in a washing vessel. Examples of suitable apparatus are described in Ullmann's Encyclopedia of Industrial Chemistry, 5th ed., CD-ROM Version, Section 3.1.1 to 3.1.5.

The present invention also provides a process for preparing acrylates by a) condensing alkanols as defined above with α,β-ethylenically unsaturated carboxylic acids or their anhydrides as defined above in an organic reaction medium and b) washing the organic phase with an aqueous washing medium in order in particular to remove excess α,β-ethylenically unsaturated carboxylic acid which comprises conducting step b) using an anionic flocculant as defined above.

Step a) is preferably conducted as described above for the preparation of polyester acrylates and polyether acrylates.

The inventive examples and comparative examples which follow illustrate the invention without restricting it to them:

GENERAL EXPERIMENTAL PROCEDURE

In a washing vessel, 3.7 liters of a reaction mixture comprising 40% by weight cyclohexane as solvent, about 55% by weight alkoxylated trimethylolpropane triacrylate and about 5% by weight acrylic acid were freed from excess acrylic acid in three washing steps: a prewash (with 1 liter), neutralization (with 0.67 liter) and a post-wash (with 1 liter) of aqueous washing medium. The washing medium employed for the prewash contained water and also NaCl to facilitate phase separation. The washing medium employed for the neutralization contained water and EarH and the washing medium employed for the post-wash contained water and NaCl. Table 1 shows four examples (1–4) for reducing the phase separation times by using anionic flocculants in a concentration of 100 or 80 ppm in all three washing steps. Table 1 also gives 4 comparative examples (C1–C4): a comparison experiment without flocculant (reference), an experiment with a nonionic flocculant, one with a cationic flocculent and one with a nonionic emulsion breaker.

It is clearly evident that the use of the anionic flocculant significantly shortens the phase separation times.

TABLE 1

| Ex. | Compound employed | Modification | Charge density[1] | Molecular weight (in millions of daltons) | Phase separation time [min] after Prewash | Neutralization | Post-wash | Total separation time |
|---|---|---|---|---|---|---|---|---|
| 1 | Sedipur[2] 402 | anionic | 4 | 12–16 | 30 | 17 | 25 | 72 |
| 2 | Sedipur AF 900 | anionic | 9 | 12–16 | 25 | 15 | 30 | 70 |
| 3 | Sedipur AF 404 100 ppm | anionic | 4 | 16–20 | 24 | 15 | 30 | 69 |
| 4 | Sedipur AF 404 80 ppm | anionic | 4 | 16–20 | 35 | 25 | 30 | 90 |
| C1 | Sedipur NF 104 | nonionic | — | 16–20 | 42 | 30 | 60 | 132 |
| C2 | Sedipur CF 104 | cationic | 3 | 10–12 | 42 | 32 | 65 | 139 |
| C3 | Separol[3] NF 34 | nonionic | — | — | 42 | 30 | 35 | 107 |
| C4 | Reference | | | | 42 | 25 | 30 | 97 |

[1] milliequivalents of Na acrylate per gram of substance
[2] Sedipur: flocculant based on acrylamide or acrylic acid
[3] Separol: emulsion breaker (propoxylated polyimine in 35% strength naphtha solution)

We claim:

1. A process comprising washing a reaction mixture by adding thereto an aqueous washing medium and separating organic and aqueous phases, wherein the reaction mixture is obtained by esterification of a α,β-ethylenically unsaturated carboxylic acid and/or anhydride component with an alcohol component selected from the group consisting of alkanols, (poly)alcohols, polyesterols and polyetherols, wherein said reaction mixture comprises monomeric acrylates, diacrylates, (poly)ester acrylates or (poly)ether acrylates, and unreacted components, and wherein said separating is carried out in the presence of at least one organic, polymeric, anionic water-soluble flocculant.

2. A process as claimed in claim 1, wherein the flocculent is selected from functional, high molecular mass polymers which comprise carboxylic acid, sulfonic acid, phosphoric acid and/or phosphonic acid functions.

3. A process as claimed in claim 1, wherein a flocculant is an anionically modified polyacrylamide.

4. A process as claimed in claim 1, wherein the anionic flocculant has a molecular weight of from 4 to 22 megadaltons.

5. A process as claimed in claim 1, wherein the anionic flocculant has a viscosity in the range from 11 to 13 mPa.s at a concentration of 0.01% by weight of polymer in fully deionized water.

6. A process as claimed in claim 1, wherein the anionic flocculant has a charge density in the range from 1 to 10 milliequivalents of sodium acrylate per g of substance.

7. A process as claimed in claim 1, wherein the anionic flocculant is employed in a concentration of from 10 to 1000 ppm, based on the aqueous phase of the organic-aqueous system.

8. A process as claimed in claim 1, wherein the organic phase of the organic-aqueous system comprises polyether acrylates.

9. A process as claimed in claim 1, wherein the organic phase of the organic-aqueous system comprises alkoxylated trimethylolpropane triacrylate.

10. A process for preparing acrylates by
   a) condensing at least one alkanol with at least one α,β-ethylenically unsaturated carboxylic acid or anhydride thereof in organic medium and
   b) washing the organic phase with an aqueous washing medium which comprises conducting step b) using a flocculant as defined in claim 1.

* * * * *

UNITED STATES PATENT AND TRADEMARK OFFICE
CERTIFICATE OF CORRECTION

PATENT NO. : 6,011,176
DATED : January 4, 2000
INVENTOR(S): Wolfgang PAULUS, ET AL.

It is certified that an error appears in the above-identified patent and that said Letters Patent is hereby corrected as shown below:

Column 3, line 18 "NaOR," should read --NaOH,--.

Column 6, line 54 "EarH" should read --NaOH--.

Column 7, line 34 "flocculent" should read --flocculant--.

Signed and Sealed this

Eighth Day of May, 2001

Attest:

NICHOLAS P. GODICI

Attesting Officer   Acting Director of the United States Patent and Trademark Office